(12) United States Patent
Bernhard-Cahill et al.

(10) Patent No.: US 12,419,766 B2
(45) Date of Patent: Sep. 23, 2025

(54) REHABILITATION DEVICE TO CORRECT POSTURE

(71) Applicant: VAMOS A LA PLAYA LLC, Rumson, NJ (US)

(72) Inventors: Susan E. Bernhard-Cahill, Rumson, NJ (US); Michael T. Kircher, Little Silver, NJ (US)

(73) Assignee: VAMOS A LA PLAYA LLC, Rumson, NJ (US)

( * ) Notice: Subject to any disclaimer, the term of this patent is extended or adjusted under 35 U.S.C. 154(b) by 395 days.

(21) Appl. No.: 17/931,819

(22) Filed: Sep. 13, 2022

(65) Prior Publication Data

US 2023/0082943 A1   Mar. 16, 2023

Related U.S. Application Data

(60) Provisional application No. 63/243,349, filed on Sep. 13, 2021.

(51) Int. Cl.
*A61F 5/01* (2006.01)
*A61F 5/02* (2006.01)

(52) U.S. Cl.
CPC ............ *A61F 5/0102* (2013.01); *A61F 5/026* (2013.01)

(58) Field of Classification Search
CPC ........ A61F 5/024; A61F 5/026; A61F 5/0102; A61F 5/37; A61G 7/07; A61G 7/072; A61G 13/121; A61G 13/00
USPC ............................................. 5/621–624, 632
See application file for complete search history.

(56) References Cited

U.S. PATENT DOCUMENTS

| | | | | |
|---|---|---|---|---|
| 3,745,996 A * | 7/1973 | Rush, Sr. | .................. | A61F 5/04 378/208 |
| 3,945,376 A * | 3/1976 | Kuehnegger | ........... | A61F 5/024 602/19 |
| 4,821,739 A * | 4/1989 | Willner | .................... | A61F 5/024 600/587 |
| 5,131,106 A * | 7/1992 | Jackson | ................. | A61G 13/00 5/607 |
| 5,966,763 A * | 10/1999 | Thomas | ................. | A61G 13/12 5/911 |
| 6,112,349 A * | 9/2000 | Connolly | ............... | A61G 7/001 5/607 |
| 6,941,951 B2 * | 9/2005 | Hubert | .................... | A61G 13/12 128/845 |

(Continued)

*Primary Examiner* — Rachael E Bredefeld
(74) *Attorney, Agent, or Firm* — Fox Rothschild LLP

(57) ABSTRACT

A device and corresponding method to position a patient's shoulders and hips into a proper posture alignment for neuromuscular re-education and rehabilitation is disclosed. The device may include a base for supporting a back of a patient, the base extending along a length in a longitudinal direction and a width in a lateral direction substantially perpendicular to the longitudinal direction. The device may include a first adjustable pad and a second adjustable pad opposite the first adjustable pad, and each of the first and second adjustable pads may be configured to independently move towards and away from the base in a vertical direction thereby urging respective shoulders of the patient against the base. The device may further include an adjustable strap configured to surround the waist and/or hips of the patient and thereby urge the patient against the base.

15 Claims, 8 Drawing Sheets

(56) References Cited

U.S. PATENT DOCUMENTS

| | | | | |
|---|---|---|---|---|
| 2002/0082531 | A1* | 6/2002 | VanBrunt | A61H 9/0078 |
| | | | | 601/41 |
| 2002/0157186 | A1* | 10/2002 | VanSteenburg | A61G 13/04 |
| | | | | 5/621 |
| 2004/0133979 | A1* | 7/2004 | Newkirk | A61F 5/3761 |
| | | | | 5/624 |
| 2008/0269030 | A1* | 10/2008 | Hoffman | A61H 1/0222 |
| | | | | 482/148 |
| 2009/0308400 | A1* | 12/2009 | Wilson | A61B 90/57 |
| | | | | 128/845 |
| 2016/0270995 | A1* | 9/2016 | Carter | A61G 13/10 |

* cited by examiner

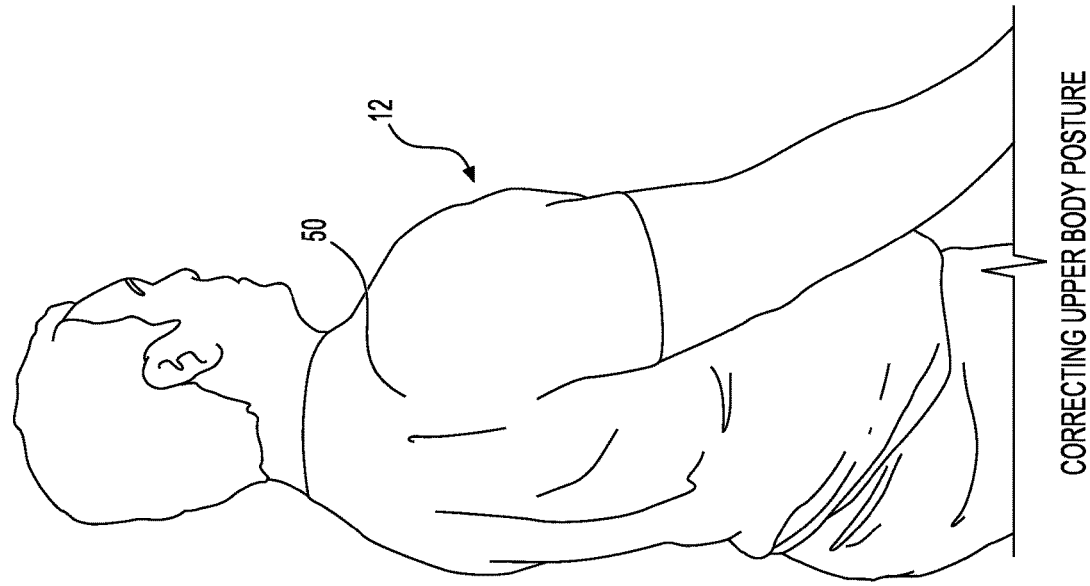
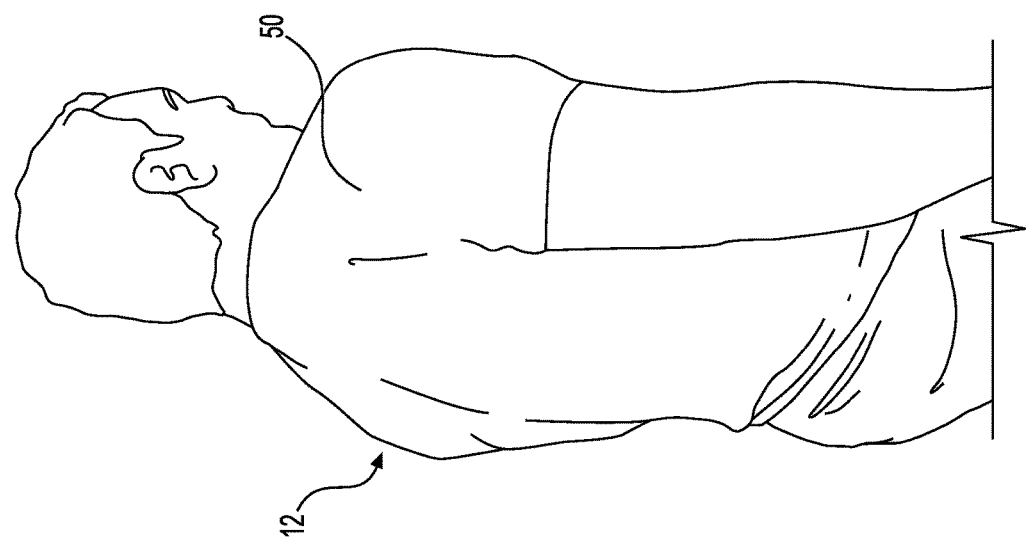

REHABILITATION DEVICE TO CORRECT POSTURE

FIELD

The present disclosure is directed to a device and corresponding method to position a patient's shoulders and hips into a proper posture alignment for neuromuscular re-education and rehabilitation.

BACKGROUND

A person with poor posture may have various underlying issues including: rounded shoulders, an over arched spine, and/or protruding abdomen among other misalignments of various sections of the body. Poor posture may lead to tension and pain in a person's neck, upper back, lower back, and shoulders. Other effects from poor posture may include poor circulation, impaired lung function, poor digestion, constricted nerves, misaligned spine, and/or problematic spine curvature. Poor posture can be the result of various different causes.

SUMMARY

In various embodiments, a device for correcting posture of a patient is disclosed. The device may include a base for supporting a back of the patient, and the base may extend along a length in a longitudinal direction and a width in a lateral direction substantially perpendicular to the longitudinal direction. In various embodiments, a first adjustable pad and a second adjustable pad opposite the first adjustable pad may be provided. Each of the first and second adjustable pads may be configured to independently move towards and away from the base in a vertical direction thereby urging respective shoulders of the patient against the base. In various embodiments, an adjustable strap configured to surround hips of the patient and thereby urge the patient's lower back against the base may be provided.

In various embodiments, the base may be formed of a rigid board.

In various embodiments, a padded cover may surround the base.

In various embodiments, a first vice supporting the first adjustable pad may be configured to move the first adjustable pad towards the base in the vertical direction; and a second vice supporting the second adjustable pad may be configured to move the second adjustable pad towards the base in the vertical direction.

In various embodiments, the first vice may include a first hand vice grip and first clamping handle and the second vice may include a second vice grip and second clamping handle.

In various embodiments, a first slidable support and a second slidable support opposite the first slidable support may be provided. In various embodiments, the first vice is coupled to the first slidable support and is configured to slide outward and inward in the lateral direction, and the second vice is coupled to the second slidable support and is configured to slide outward and inward in the lateral direction.

In various embodiments, the first vice comprises a first pneumatically operated compression vice including a first compression cylinder and a first release valve, and the second vice comprises a second pneumatically operated compression vice including a second compression cylinder and a second release valve.

In various embodiments, a first slidable support and a second slidable support opposite the first slidable support may be provided. In various embodiments, the first vice is coupled to the first slidable support and is configured to slide outward and inward in the lateral direction, and the second vice is coupled to the second slidable support and is configured to slide outward and inward in the lateral direction.

In various embodiments, the base may include a first portion and a second portion, the second portion including at least one sliding arm that is configured to move forward and backward within a corresponding aperture of the first portion. Additionally, in various embodiments, the at least one sliding arm may include a first indicator configured to visually display how far apart the first portion and second portion are spread apart from one another. Additionally, in various embodiments, the first adjustable pad and the second adjustable pad may include a second indicator configured to visually display how far apart the first adjustable pad and/or second adjustable pad are spread apart from a neutral position.

In various embodiments, the first and second adjustable pads are positioned to press down on a front side of a patient's upper chest, which upper chest includes the front side of the patient's shoulders.

In various embodiments, the device is configured to support a patient in a supine position.

In various embodiments, the device may include a seat for supporting a buttocks of the patient, the base extends upwardly from the seat, and the device is configured to support the patient in an upright seating position.

In various embodiments, a device for correcting posture of a patient is disclosed. The device may include, a substantially planar T-shaped base having a first portion and a second portion. The first portion having a size and shape for supporting a back of a patient and the second portion having a size and shape for supporting a lower back of a patient, around the waist and hips area. In various embodiments, the base may extend along a length in a longitudinal direction that defines a centerline of the base and extend along a width in a lateral direction substantially perpendicular to the longitudinal direction. In various embodiments, a first adjustable pad and a second adjustable pad disposed on opposite sides of the centerline of the base may be provided. In various embodiments, each of the first and second adjustable pads may be configured to directly contact respective upper chest portions of the patient, a first vice may support the first adjustable pad and be configured to move the first adjustable pad towards the base in the vertical direction, and a second vice may support the second adjustable pad and be configured to move the second adjustable pad towards the base in the vertical direction. In various embodiments, the device may further include a first side rail and a second side rail disposed on opposite sides of the centerline and an adjustable strap slidably coupled to the first side rail and the second side rail may be provided. This adjustable strap may permit movement in the longitudinal direction, and the adjustable strap may be configured to surround the hips of the patient and thereby urge and/or secure the patient against the base.

In various embodiments, the first vice includes a first hand vice grip and a first clamping handle and the second vice comprises a second vice grip and a second clamping handle.

In various embodiments, a first slidable support and a second slidable support opposite the first slidable support may be provided. Additionally, the first vice may be coupled to the first slidable support and may be configured to slide outward and inward in the lateral direction. In various embodiments, the second vice is coupled to the second slidable support and is configured to slide outward and inward in the lateral direction.

In various embodiments, the first vice may include a first pneumatically operated compression vice including a first compression cylinder and a first release valve, and the second vice may include a second pneumatically operated compression vice including a second compression cylinder and a second release valve.

In various embodiments, a first slidable support and a second slidable support opposite the first slidable support may be provided. Additionally, the first vice may be coupled to the first slidable support and may be configured to slide outward and inward in the lateral direction, and the second vice may be coupled to the second slidable support and may be configured to slide outward and inward in the lateral direction.

In various embodiments, a device for correcting a patient's posture is disclosed. The device may include a base, an adjustable pad configured to force a backside of the patient's shoulders against the base, and an adjustable strap configured to go around the hips to hold a patient's lower back against the base.

In various embodiments, the adjustable pad may include at least two pads.

In various embodiments, a method of correcting poor posture is disclosed. The method may include the step of providing: a device for correcting posture of a patient is disclosed. The device may include a base for supporting a back and waist of a patient, and the base may extend along a length in a longitudinal direction and a width in a lateral direction substantially perpendicular to the longitudinal direction. In various embodiments, a first adjustable pad and a second adjustable pad opposite the first adjustable pad may be provided. Each of the first and second adjustable pads may be configured to independently move towards and away from the base in a vertical direction thereby urging respective shoulders of the patient against the base. In various embodiments, an adjustable strap configured to surround the hips of the patient and urge the patient against the base may be provided. The method may further include the step of placing the back of the patient against the base. The method may further include the step of moving, independently, the first adjustable pad and the second adjustable pad against the patient's upper chest to thereby urge the back side of the shoulders against the base; and maintaining the position of the patient's back for a pre-determined amount of time.

BRIEF DESCRIPTION OF THE DRAWINGS

FIG. 1A is an illustration showing a person with a poor upper body posture;

FIG. 1B is an illustration showing a person with a corrected upper body posture;

DETAILED DESCRIPTION OF THE DISCLOSURE

The present disclosure is described with reference to the attached figures, in which like numerals represent like items throughout the figures. The figures may not be drawn to scale and are provided to illustrate various aspects and embodiments in accordance with the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details or may be implemented with other methods not explicitly disclosed herein. In other instances, well-known structures or operation may not be shown in detail to avoid obscuring the most important features of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

FIG. 1A is an illustration showing a person 12 with hunched forward shoulders 50 illustrating a posture that may be generally categorized as a poor upper body posture. The person 12 is hunched with the neck in an unnaturally forward position. FIG. 1B is an illustration showing a person 12 with a posture in which the shoulders 50 are positioned such that the patients posture may be generally categorized as good upper body posture. The person 12 stands tall with chest out and neck extended upwardly.

Figure 2:
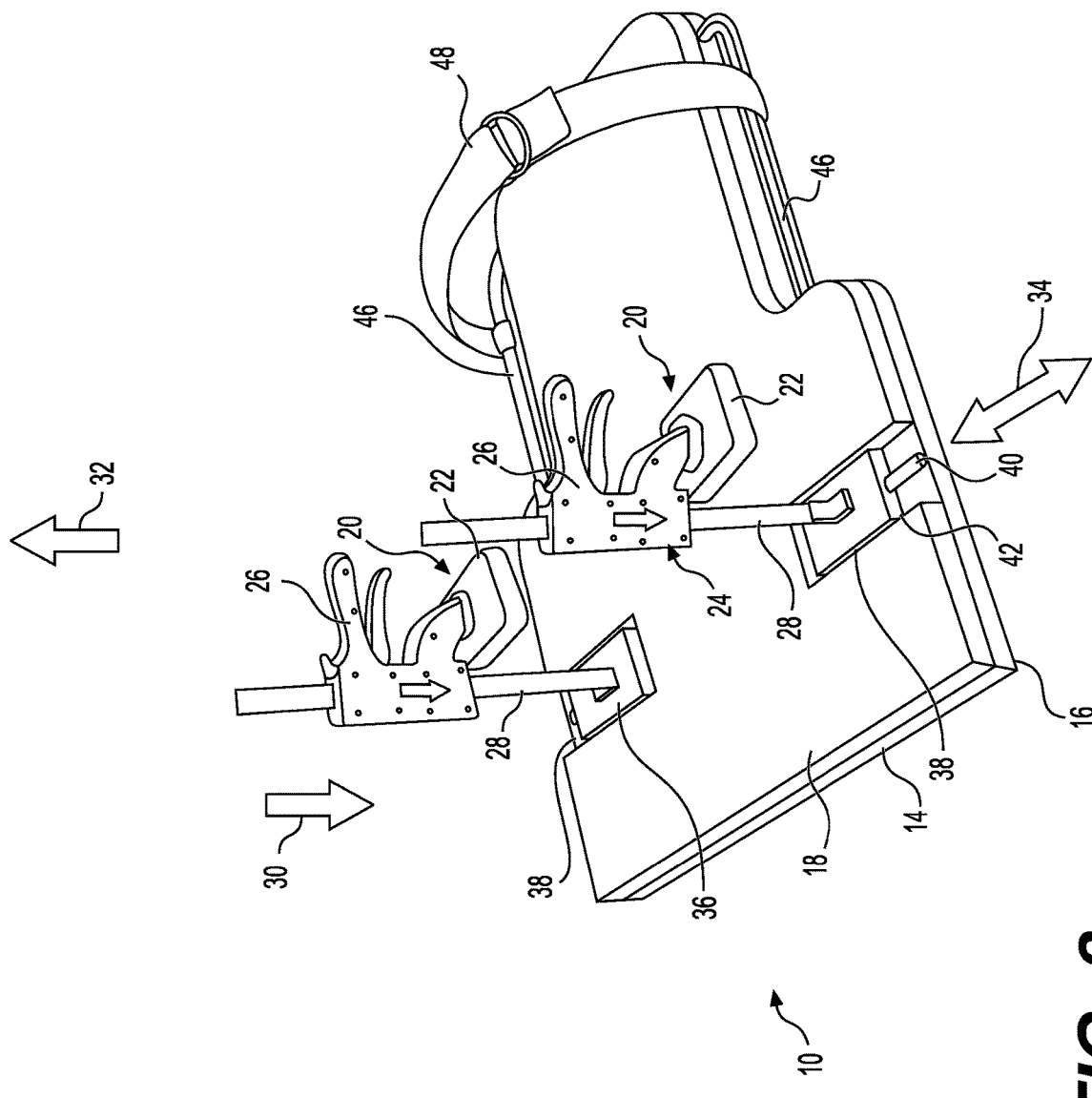
FIG. 2 is a perspective view of a device for correcting a patient's posture.

With reference to FIG. 2, a first embodiment of the present disclosure is now described. A posture correcting device 10 for correcting posture of a person/patient 12 is shown. In various embodiments, the device 10 includes a substantially flat and/or substantially planar base 14 on which the patient may lay (see FIG. 3) to keep the patient's back flat. The base 14 can be formed of a rigid board 16 made of a rigid material such as wood, metal, or plastic. In various embodiments, the base 14 may include a padded cover 18 for comfortably supporting the patient 12. In the example embodiment, the base 14 is a T-shaped base in which the top portion is wider to accommodate the patient's shoulders and the lower portion is narrower to accommodate the patient's lower back and hips.

In the example embodiment, adjustable shoulder pads 20 are provided to push/hold down the patient's shoulders 50 against the base 14. In one embodiment, the adjustable shoulder pads 20 are formed as rubber pads 22, configured for patient comfort, attached to vice mechanisms 24 (may also be referred to as a clamp 24). In various embodiments, the vice mechanism 24 may be formed as a hand operated vice grips 26 moveable over a shaft 28 downwardly in a vertical direction towards base 14 (visually represented by arrow 30) by operation of the handgrips 26 and associated lever. For example, handgrips 26 can be released to allow vertical upward movement (visually represented by arrow 32) away from base 14. Handgrips 26 may take any suitable form or use any suitable means for movably supporting adjustable shoulder pads 20 for holding and/or urging the patient's shoulders against the base 14.

In various embodiments, the vice mechanisms 24 may be further adjustable in a lateral direction as indicated by arrow 34 to accommodate the patient's shoulder width. In the example embodiment, the shaft 28 of each of the vice mechanisms 24 may be attached to a slidable support 36 that is configured to slide in a lateral direction towards and/or away from a centerline of the base 14. In various embodiments, slidable support 36 may be configured to slide outward in a lateral direction away from base 14. For example, each slidable support 36 may be disposed on opposite lateral sides of base 14 and be movable and/or slidable in the directions 34. For example still, each slidable support 36 may be disposed within a cutout 38 in the padded cover 18 (or base 14) and include an aperture or recess 42 therein in which a slide bar 40 is disposed. The slide bar 40 may be securely coupled to and/or attached to the rigid board 16, which cooperates with the recess 42 in the bottom of the slidable support 36.

Figure 3:
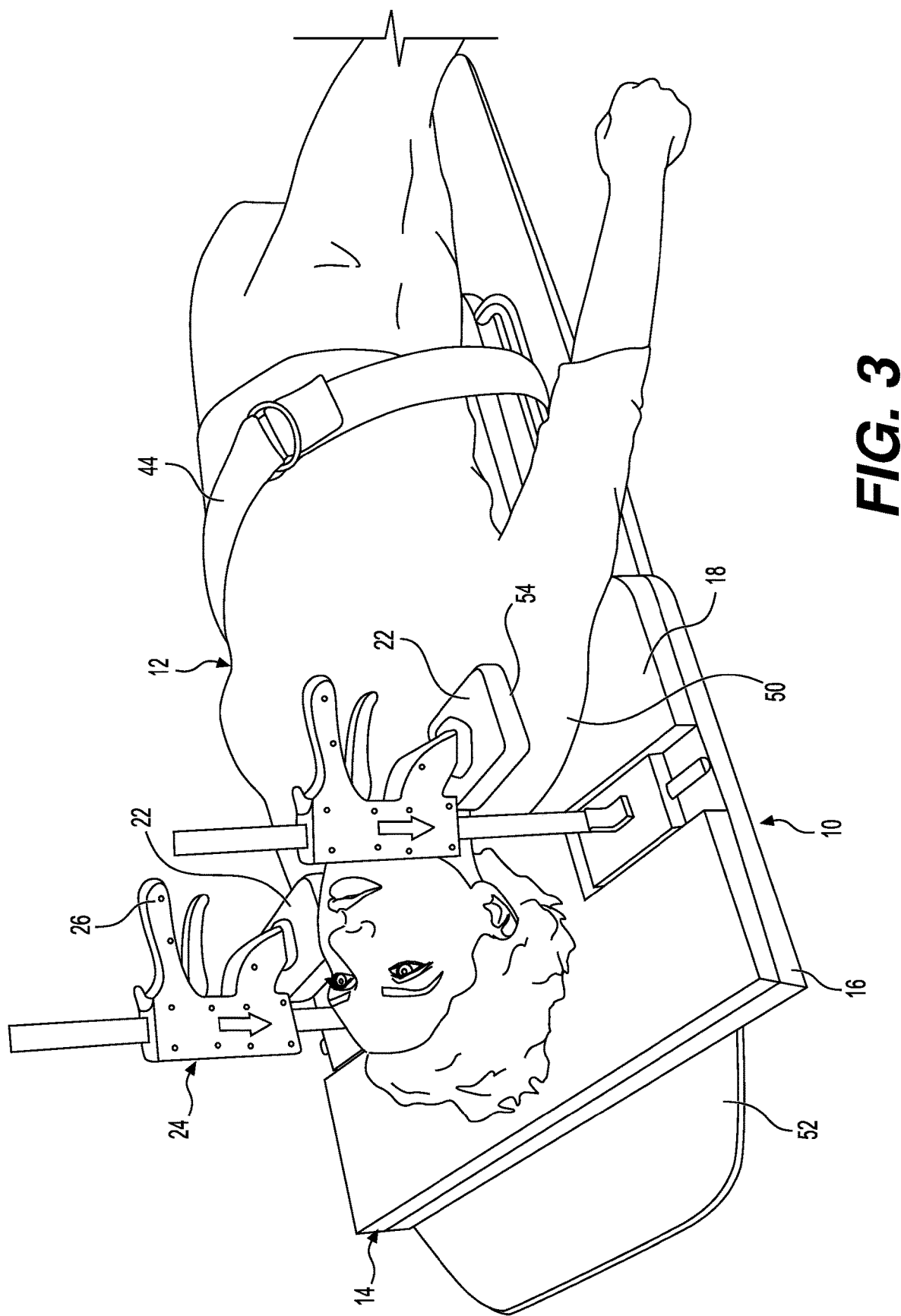
FIG. 3 illustrates the device of FIG. 2 in use with a patient.
Figure 4:
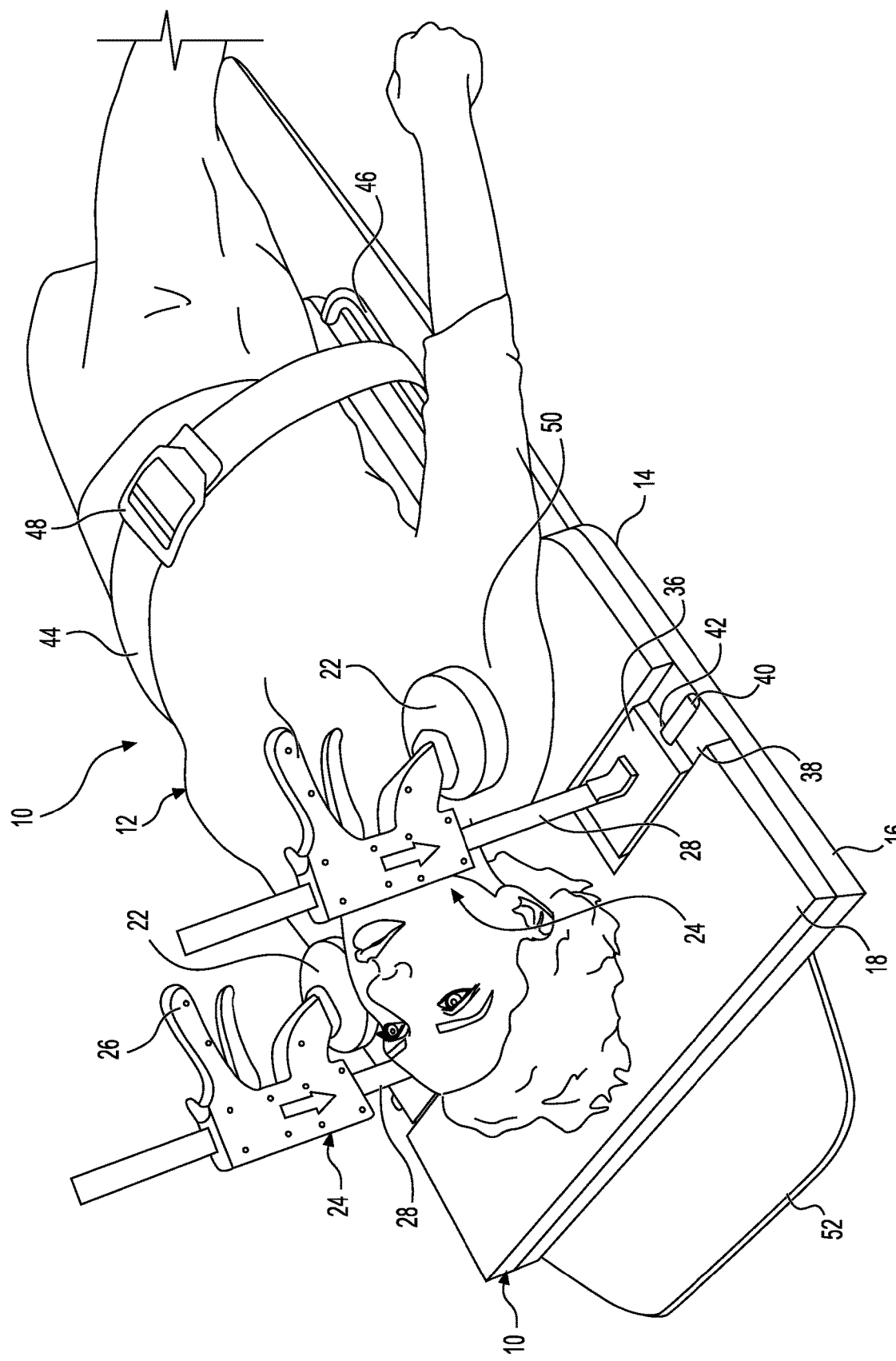
FIG. 4 is a perspective view of a second embodiment of a device for correcting a patient's posture being used with a patient.

In various embodiments, an adjustable belt/strap 44 is provided around the hips to hold the patient's lower back flat against the base 14. In the illustrated embedment, the belt 44 is attached to side rails 46, which in turn are attached to the rigid board 16. In the example embodiment, the side rails extend in a longitudinal direction and allow the belt/strap to move forward and backward in a longitudinal direction of the base 14 so that the belt strap 44 may be positioned at an optimal position relative to the patient. In at least one embodiment, an optimal position may refer to having the belt/strap directly adjacent a patient's hips while they are using the device, e.g., as shown in FIGS. 3-4. The belt/strap 44 may be adjustable by any suitable means such as a buckle 48 and/or straps and Velcro connection.

With further reference to FIG. 3, an example method of use of the device 10 is now described with reference to the structural features. The device 10 can be positioned on a flat surface such as a table 52 as shown or on the floor, e.g. The patient 12 may lay down on the base 14 as shown such that the spine of the patient extends in a longitudinal direction of the device 10. A provider, such as a physical therapist, trainer, assistant, and/or chiropractor may strap the patient 12 at or below the waist via belt/strap 44 to keep the hips and pelvis neutral and the patient's back side against the base 14 as shown. For example, the belt/strap 44 may urge the patient's waist and/or back against the base 14 by applying a force against the anterior side of the patient such that a posterior side of the patient directly contacts base 14. The patient 12 may then be instructed to relax and lower/drop his/her shoulders 50 down against the base 14. The provider may adjust the shoulder pads 20 in a lateral direction to accommodate a patient's specific shoulder width. Additionally, the provider may move the adjustable shoulder pads 20 downwardly in a vertical direction, e.g., by using the hand vice grips 26, so that the pads 20 press just below the front 54 of the shoulders 50, or the upper chest area, thereby forcing and/or urging both shoulders 50 against the base 14. In one example, the patient 12 may stay in this position for 10-15 minutes. In another example, the patient 12 may stay in this position for as long as is reasonably comfortable, e.g., 5 minutes, 10 minutes, 15 minutes, 30 minutes, an hour, etc. Due to the positioning of the device 10, the pectoral muscles of the patient may stretch, and the patient may be urged into and/or experience a feeling embodying the optimal posture he/she should be in at all times (see e.g., FIG. 1B).

After the patient has been urged into the optimal position for a period of time, the shoulder pads 20 may be removed by the provider. For example, the vice mechanism 24 may be released. Over time and with repeated use, the patient 12 may have trained his/her shoulders 50, pectoral muscles, neck, back, and/or hips to be in the proper posture positioning (see, e.g., FIG. 1B).

A second embodiment is now described with reference to FIG. 4. The embodiment of FIG. 4 may include the same, similar, and/or substantially the same features and functionality as explained above with respect to the other embodiments. The device 10 shown in FIG. 4 may contain like reference numbers referencing similar elements, a description of which may not be repeated herein for brevity and ease of explanation. In the embodiment of FIG. 4, rounded shoulder pads 22, made of a comfortable material, are provided. In one example, a foam material and/or pliable gel like material may be provided however other material choices that are flexible and/or pliable may also be used. Like the embodiment of FIG. 3, this embodiment is operated in a similar manner with a patient 12 lying in a supine position with a posterior side of the patient lying flat and directly against the base 14.

Figure 5:
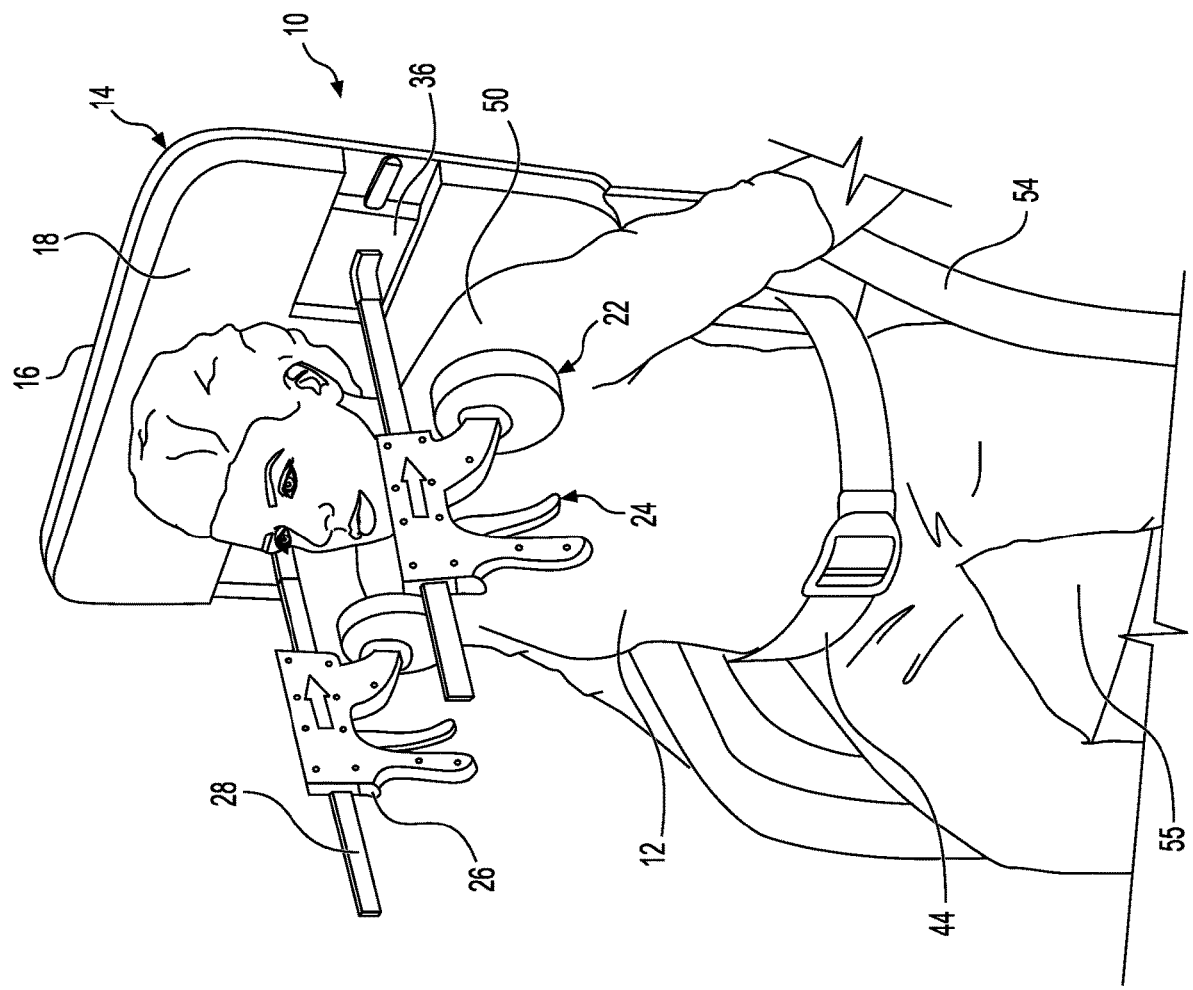
FIG. 5 is a perspective view of third embodiment of a device for correcting a patient's posture being used with a patient.

A third embodiment is now described with reference to FIG. 5. The embodiment of FIG. 5 may include the same, similar, and/or substantially the same features and functionality as explained above with respect to the other embodiments. The device 10 shown in FIG. 5 is illustrated with like reference numbers referencing similar elements. This embodiment, however, is configured for use with the patient 12 in an upright position as shown (rather than the supine position of FIGS. 3 and 4). The device 10 can be positioned against the back of a chair 74 and held in place and/or coupled thereto by various means such as straps (not shown). In one embodiment, the device 10 may be formed as part of the chair 74, e.g., the base may form the back portion of a chair 74 and extending upwardly from the seat 55 of the chair 74. In various embodiments, the device 10 may extend substantially perpendicular from a surface of the seat 55 as shown. In use, the patient 12 may sit in the chair with his/her back against the base 14 and be strapped to the device 10 at or below the waist via strap 44 as shown. The patient 12 may position his/her shoulders 50 against the base 14. As illustrated, vice mechanism 24 may include a hand operated vice grips as shown. In use, the vice mechanism 24 may be operated to press and/or urge the pads 20 against the patient's upper chest area, thereby urging the area just below the front 54 of the patient's shoulders 50 against the base 14. The patient 12 may stay in this position for 5-15 minutes, or longer as explained previously. The pectoral muscles of the patient may stretch, and the patient may be urged into and/or experience a feeling embodying the optimal posture he/she should be in at all times (see e.g., FIG. 1B).

After the patient has been urged into the optimal or posture correct position for a period of time, the shoulder pads 20 may be removed, e.g., by releasing the vice mechanism 24. Over time and with repeated use, the patient 12 may have trained his/her shoulders 50, pectoral muscles, neck, back, and/or hips to be in the proper posture positioning (see, e.g., FIG. 1B).

Figure 6:
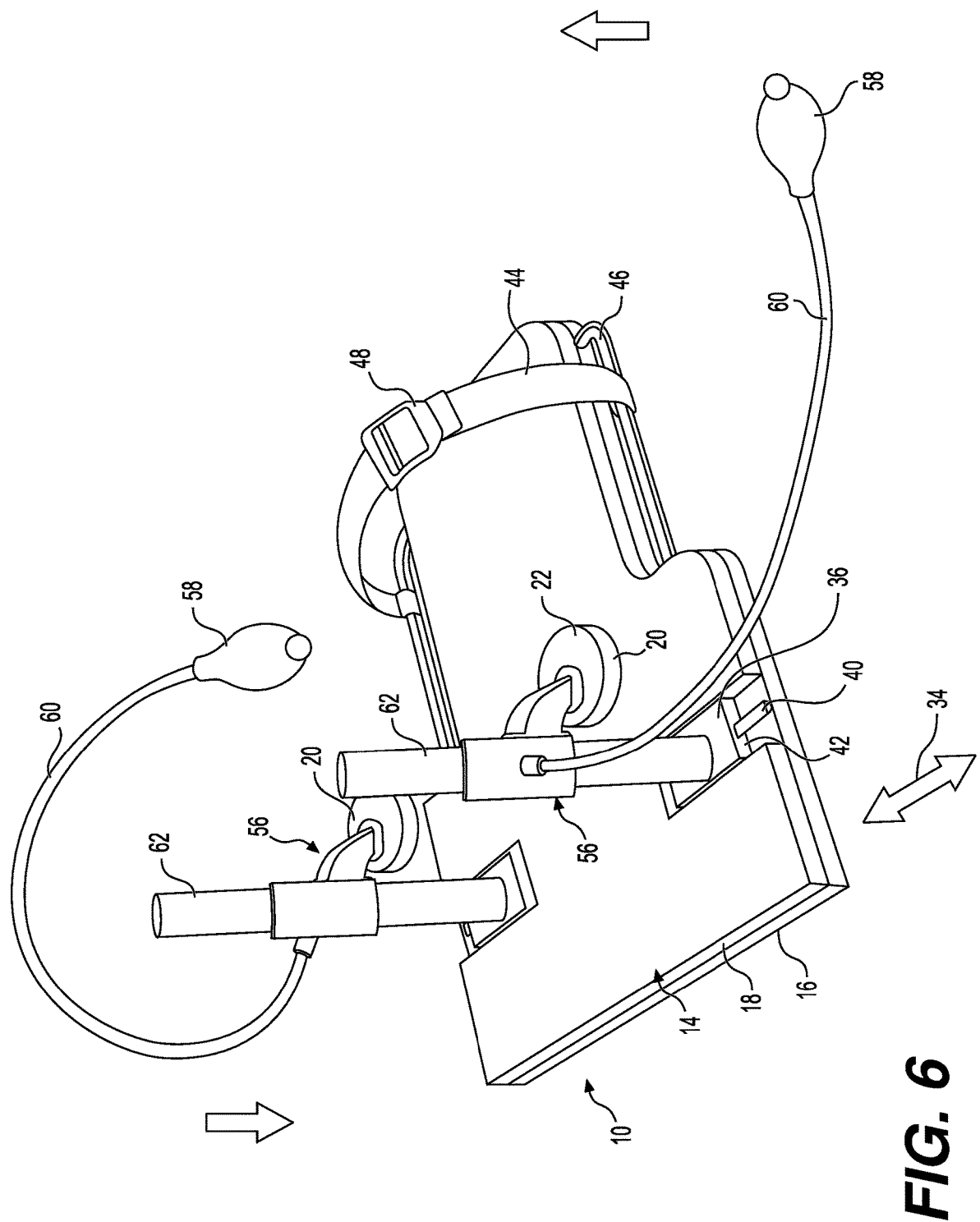
FIG. 6 is a perspective view of a fourth embodiment of a device for correcting a patient's posture being used with a patient.

A fourth embodiment is now described with reference to FIG. 6. The embodiment of FIG. 6 may include the same, similar, and/or substantially the same features and functionality as explained above with respect to the other embodiments. The device of FIG. 6 may include like reference numbers referencing similar elements for ease of understanding and explanation. The device 10 shown in FIG. 6 is similar to the embodiments of FIGS. 3-5 as described above, and includes an alternative type of vice mechanism 24. In the embodiment of FIG. 6, the vice mechanism 24 is formed as a pneumatic vice 56 for urging the pads 20 against the upper chest area of the patient. For example, vice 56 may be referred to as a pneumatic compression device that operates under similar principles as explained above but with different relative advantages such as, for example, micro-adjustments and ease of use by the patient him or herself. In this embodiment, a pair of pneumatic compression vices 56 are included and each pneumatic compression vice 56 may include a pneumatic pressure bulb 58. Each corresponding pressure bulb 58 may be repeatedly squeezed to provide pressurized air through tubes 60 to pneumatic cylinders within each of the support arms 62 to move the pads 22 downwardly towards the base 14. In this way, each instance in which the pressure bulb 58 is squeezed air is compressed and provides a force urging the pads 22 towards the base 14. In various embodiments, a pressure release button 64 (and/or pressure release valve 64) can be pressed/actuated to release the compressed air within the cylinders thereby allowing the pads 22 to release any applied force against the patient 12. For example, the pads 22 may return to their upward position and/or at least a neutral position in which no significant force is applied to the patient. This embodiment may be operated in a similar manner as that of the previous embodiments, with the exception that the pressure bulb 58 is operated to move the shoulder pads 22 rather than the clamp portions of vice 24. The pneumatic compression device allows the patient to urge the pads 22 against his or her upper chest and towards the base 14 without the assistance of a provider or another person.

Figure 7:
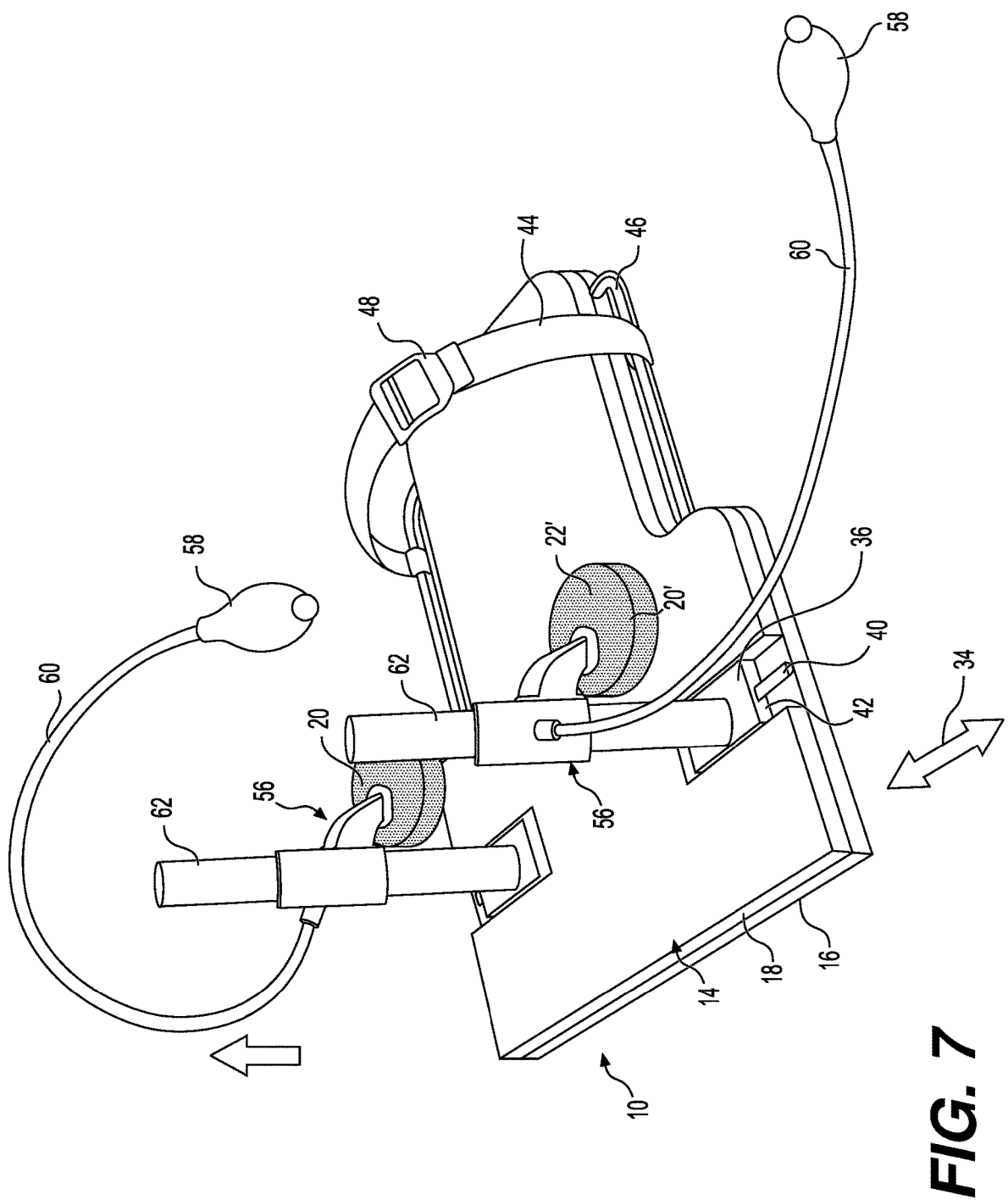
FIG. 7 is a perspective view of a fifth embodiment of a device for correcting a patient's posture being used with a patient.

A fifth embodiment is now described with reference to FIG. 7. The embodiment of FIG. 7 may include the same, similar, and/or substantially the same features and functionality as explained above with respect to FIG. 6. The device of FIG. 7 may include like reference numbers referencing similar elements for ease of understanding and explanation. The device 10 shown in FIG. 7 may include a thermal pad 22' which replaces and/or surrounds pad 22 shown in FIG. 6. In this embodiment, the thermal pad 22' may be, for example, a cold pack and/or a heat pack. In one method of use, a provider may slide a cold thermal pad 22' over the shoulder pad 22 (see FIG. 6). This embodiment has the advantage of providing a cold compress to alleviate inflammation and/or swelling. In another embodiment, the provider may slide a hot thermal pad 22' over the shoulder pad 22 (see FIG. 6). This embodiment has the advantage of providing heat to the patient which may help loosen and/or stretch contracted muscles e.g., the pectoral muscles. Additionally, in various embodiments, the provider may utilize a cold thermal pad 22' for a period of time and then replace the cold thermal pad 22' with a hot thermal pad 22' (or vice versa).

Another embodiment is contemplated that is lighter, and preferred for use at home/office/gym/airport, etc. In this lighter version embodiment, the squeeze handles of the vice mechanism 24 can be positioned so that the patient 12 can independently operate the adjustable shoulder pads 20 without the need of a provider. This device 10 can be used both lying down or sitting in a straight-back chair similar to the above explained embodiments. As with the embodiments described above, the benefits of shoulder training, pectoral muscle stretch and hip alignment may be achieved, thereby enabling the patient 12 to attain the proper posture positioning (see FIG. 1B).

Figure 8:
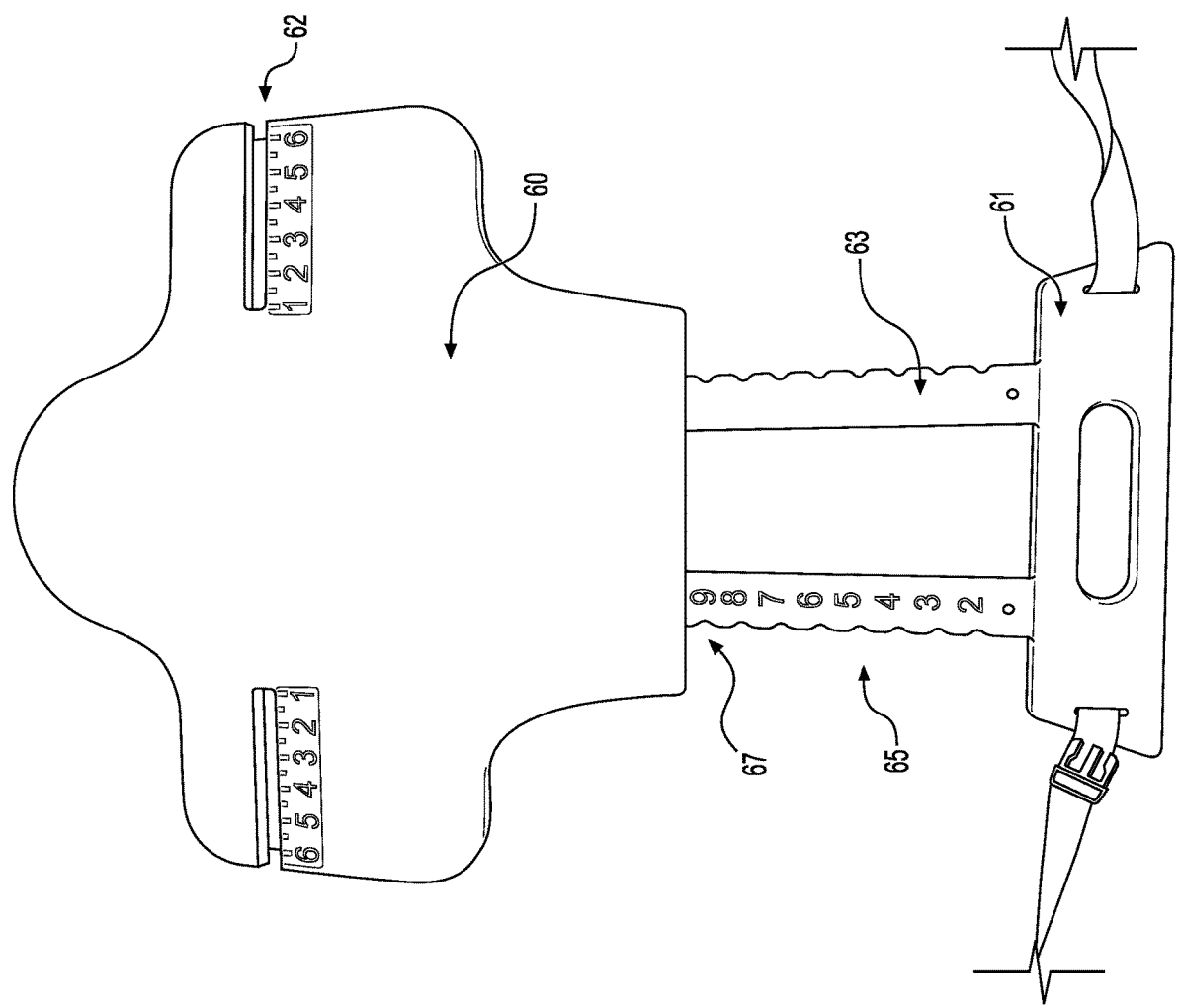
FIG. 8 is a top plan view of a sixth embodiment of a device for correcting a patient's posture.

FIG. 8 is a top plan view of a sixth embodiment of a device for correcting a patient's posture, and which is preferred for use with a chair or seat. The embodiment of FIG. 8 may include the same, similar, and/or substantially the same features and functionality as explained above with respect to the previous embodiments. In the example embodiment, a rigid base 60 may include a pair of cutouts 62 in which respective slidable supports 36 may be disposed. In this embodiment, cutout 62 permits the slidable support 36 to slide in a lateral direction towards and/or away from a centerline of the base 62. In addition, each cutout includes an indicator showing how far away from a neutral position a respective slidable support 62 is disposed. In this embodiment, each indicator features 6 positions labeled from 1-6 with half marks therebetween. This embodiment has the advantage of facilitating the centering of a patient with respect to the rigid base 60. It also has the advantage of allowing a patient to determine an optimal position of the slidable supports 36 and to utilize this optimal position for subsequent posture correcting procedures.

In the example embodiment of FIG. 8, a slidable base portion 61 may be provided. In this example, slidable base portion 61 includes a carrying handle as shown and a first and second height adjusting arm 63. Each height adjusting arm 63 may slide forward and backward within a corresponding aperture 67 of the base portion 61. Additionally, at least one of the height adjusting arms 63 may include an indicator showing the position or height of the first and second height adjusting arms 63. In the example embodiment, the indicator 65 features 10 positions with position 1 being a fully closed position and position 10 being a fully extended position. This embodiment has the advantage of allowing a patient to determine an appropriate height and/or distance to position the slidable supports. For example, with reference back to the embodiment of FIG. 5, a patient can extend a height of the rigid base 60 such that the slidable supports 36 are at an optimal height and or distance away from the adjustable strap 44.

While the disclosure has been described in terms of various example embodiments with reference to the FIGS., variations may be applied to the apparatus, methods, and sequence of steps of the method without departing from the concept, spirit, and scope of the disclosure. More specifically, it may be apparent to those of skill in the art that that certain components may be added to, combined with, eliminated, and/or substituted with the components described herein while the same or similar results may still be achieved. All such similar substitutes and modifications apparent to those skilled in the art are deemed to be within the spirit, scope, and concept of the disclosure as defined.

What is claimed is:

1. A device for correcting posture of a patient, comprising:
 a base for supporting a back of a patient, the base extending along a length in a longitudinal direction and a width in a lateral direction substantially perpendicular to the longitudinal direction;
 a first compression vice and a second compression vice opposite the first compression vice, each of the first and second compression vices comprise: a corresponding shaft extending away from the base in a vertical direction that is substantially perpendicular to a plane of the base, a corresponding compression handle, and a corresponding pad configured to directly contact a respective upper chest portion of the patient;
 wherein each corresponding compression handle and pad are configured to independently move along the shaft and towards the base in the vertical direction by squeezing the compression handle and thereby moving the pad down along the shaft to pushing a respective upper chest portion of the patient downward in the vertical direction against the base; and an adjustable strap configured to surround the waist and/or hips of the patient and thereby urge the patient against the base.

2. The device of claim 1, wherein the base is formed of a rigid board.

3. The device of claim 2, further comprising a padded cover surrounding the base.

4. The device of claim 1, further comprising:
a first slidable support and a second slidable support opposite the first slidable support, the first slidable support being directly coupled to the shaft of the first compression vice and the second slidable support being directly coupled to the shaft of the second compression vice;
wherein the first slidable support is configured to slide outward and inward in the lateral direction thereby moving the shaft of the first compression vice outward and inward in the lateral direction, and
wherein the second slidable support is configured to slide outward and inward in the lateral direction thereby moving the shaft of the second compression vice outward and inward in the lateral direction.

5. The device of claim 1 wherein the first compression vice comprises a first pneumatically operated compression vice including a first compression cylinder and a first release valve, and the second compression vice comprises a second pneumatically operated compression vice including a second compression cylinder and a second release valve.

6. The device of claim 5, further comprising:
a first slidable support and a second slidable support opposite the first slidable support, the first slidable support being directly coupled to the shaft of the first compression vice and the second slidable support being directly coupled to the shaft of the second compression vice;
wherein the first slidable support is configured to slide outward and inward in the lateral direction thereby moving the shaft of the first compression vice outward and inward in the lateral direction, and
wherein the second slidable support is configured to slide outward and inward in the lateral direction thereby moving the shaft of the second compression vice outward and inward in the lateral direction.

7. The device of claim 1, wherein
the base includes a first portion and a second portion, the second portion including at least one sliding arm that is configured to move forward and backward within a corresponding aperture of the first portion;
the at least one sliding arm including a first indicator configured to visually display how far apart the first portion and second portion are spread apart from one another; and
at least one of the first adjustable pad and the second adjustable pad include a second indicator configured to visually display how far apart the first adjustable pad and/or second adjustable pad are spread apart from a neutral position.

8. The device of claim 1, wherein the device is configured to support a patient in a supine position.

9. The device of claim 1, further comprising:
a seat for supporting a buttocks of the patient,
wherein the base extends upwardly from the seat, and
wherein the device is configured to support the patient in an upright seating position.

10. A device for correcting posture of a patient, comprising:
a substantially planar T-shaped base having a first portion and a second portion, the first portion having a size and shape for supporting a back of a patient and the second portion having a size and shape for supporting a lower back of a patient, the base extending along a length in a longitudinal direction that defines a centerline of the base and extending along a width in a lateral direction substantially perpendicular to the longitudinal direction;
a first compression vice and a second compression vice opposite the first compression vice, each of the first and second compression vices comprises: a corresponding shaft extending in a vertical direction that is substantially perpendicular to a plane of the T-shaped base, a corresponding compression handle, and a corresponding pad configured to directly contact a respective upper chest portion of the patient;
wherein each corresponding compression handle and pad are configured to independently move along the shaft and towards the base in a vertical direction by squeezing the compression handle and thereby moving the pad down along the shaft to pushing a respective upper chest portion of the patient downward in the vertical direction against the base;
a first side rail and a second side rail disposed on opposite sides of the centerline; and
an adjustable strap slidably coupled to the first side rail and the second side rail thereby permitting movement in the longitudinal direction, the adjustable strap being configured to surround the hips of the patient, the adjustable strap including a buckle configured to allow tightening of the adjustable strap to urge a waist and/or hips of the patient against the base.

11. The device of claim 10, further comprising:
a first slidable support and a second slidable support opposite the first slidable support,
wherein the first compression vice is coupled to the first slidable support and is configured to slide outward and inward in the lateral direction, and
wherein the second compression vice is coupled to the second slidable support and is configured to slide outward and inward in the lateral direction.

12. The device of claim 10, wherein the first compression vice comprises a first pneumatically operated compression vice including a first compression cylinder and a first release valve, and the second compression vice comprises a second pneumatically operated compression vice including a second compression cylinder and a second release valve.

13. The device of claim 12, further comprising:
a first slidable support and a second slidable support opposite the first slidable support,
wherein the first compression vice is coupled to the first slidable support and is configured to slide outward and inward in the lateral direction, and
wherein the second vice is coupled to the second slidable support and is configured to slide outward and inward in the lateral direction.

14. A method of correcting poor posture, comprising:
providing the device of claim 1;
placing the back of the patient against the base;
moving, independently, the first adjustable pad and the second adjustable pad against the patient's upper chest to thereby urge the back side of the shoulders against the base; and maintaining the position of the patient's back for a pre-determined amount of time.

15. A method of correcting poor posture, comprising:
providing the device of claim 1;
placing the back of the patient against the base;
tightening the adjustable strap to urge waist and/or hips of the patient against the base;
moving, independently, the first compression vice and the second compression vice into position above the patient's upper shoulders by adjusting first and second slidable supports in the lateral direction;
squeezing, independently and after the tightening and moving steps, the compression handles of the first and second compression vices to thereby apply a downward compression force against the patient's shoulders;
maintaining the downward compression force against the patient's upper chest for a time period.

\* \* \* \* \*